United States Patent [19]

Hagen et al.

[11] 4,301,157
[45] Nov. 17, 1981

[54] THIOLPHOSPHORIC ACID-S-4-NITRO-2-TRICHLOROMETHYL-PHENYL ESTERS AS FUNGICIDES

[75] Inventors: Helmut Hagen, Frankenthal; Ernst-Heinrich Pommer, Limburgerhof; Wolfgang Reuther, Heidelberg; Hans Ziegler, Frankenthal, all of Fed. Rep. of Germany

[73] Assignee: BASF Aktiengesellschaft, Fed. Rep. of Germany

[21] Appl. No.: 81,060

[22] Filed: Oct. 2, 1979

[30] Foreign Application Priority Data

Oct. 18, 1978 [DE] Fed. Rep. of Germany ....... 2845329

[51] Int. Cl.³ ...................... A01N 57/06; C07F 9/165
[52] U.S. Cl. ..................................... 424/218; 260/954
[58] Field of Search ....................... 260/954, 964, 904; 424/218

[56] References Cited

U.S. PATENT DOCUMENTS 3,274,051 9/1966 Kado et al. .......................... 424/218
3,792,132 2/1974 Bernhart .............................. 260/954
3,825,633 7/1974 Tsuchiya et al. ................... 260/956

OTHER PUBLICATIONS

Chem. Week. Jun. 21, 1972, p. 46.
Thomson, "Agri. Chemicals", vol. IV, (1976/1977), revised edition, pp. 102-103.

Primary Examiner—Anton H. Sutto
Attorney, Agent, or Firm—Keil & Witherspoon

[57] ABSTRACT

New thiolphosphoric acid-S-4-nitro-2-trichloromethyl-phenyl esters of the formula

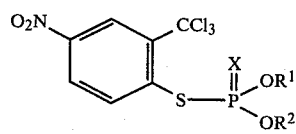

where X denotes oxygen or sulfur, and $R^1$ and $R^2$ are identical or different and each denotes a substituted or unsubstituted aliphatic radical of 1 to 18 carbon atoms or a substituted or unsubstituted alicyclic radical of 5 to 18 carbon atoms, processes for their manufacture, fungicides containing these compounds as active ingredients, their manufacture, and processes for combating fungi with these novel compounds.

4 Claims, No Drawings

THIOLPHOSPHORIC ACID-S-4-NITRO-2-TRICHLOROMETHYLPHENYL ESTERS AS FUNGICIDES

The present invention relates to new and valuable thiolphosphoric acid-S-4-nitro-2-trichloromethylphenyl esters, processes for their manufacture, and their use as fungicides, microbicides. insecticides and bactericides.

It has been disclosed to use thiolphosphoric acid-O,O-diisopropyl-S-benzyl ester (W. T. Thomson, Agricultural Chemicals IV, Fungicides, Indianapolis, Indiana, 1973) and dithiophosphoric acid-O-butyl-S-benzyl-S-ethyl ester (U.S. Pat. No. 3,825,633) as fungicides.

We have now found compounds which have a good action on injurious fungi and possess a wider spectrum of action.

The object of the invention is to provide novel thiolphosphoric acid-S-4-nitro-2-trichloromethylphenyl esters of the formula

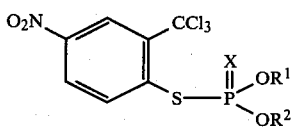

I where X denotes oxygen or sulfur, and $R^1$ and $R^2$ are identical or different and each denotes a substituted or unsubstituted aliphatic radical of 1 to 18 carbon atoms, or a substituted or unsubstituted alicyclic radical of 5 to 18 carbon atoms.

Examples of meanings for $R^1$ and $R^2$ are methyl, ethyl, isopropyl, n-propyl, n-hexyl, n-octyl and n-dodecyl. Particularly suitable substituents on the aliphatic radicals are hydroxyl; halogen, preferably fluorine, chlorine and bromine; alkoxyl, preferably of 1 to 4 carbon atoms; carboxyl, preferably of 2 to 20 carbon atoms; and carbalkoxy, preferably of 2 to 10 carbon atoms. Examples of substituted alkyl radicals are methoxyethyl, hydroxyethyl and stearyl.

Particularly suitable alicyclic radicals are cycloalkyl radicals which may be substituted in the same manner as above.

A further object of the invention is to provide a process for the manufacture of compounds of the formula I, wherein (a) 4-nitro-2-trichloromethylbenzenesulfenic acid chloride is reacted in an inert solvent with a phosphorous acid dialkyl ester of the formula

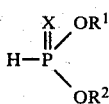

II where $R^1$, $R^2$ and X have the above meanings, at from −40° to +120° C., or (b) when X is oxygen and $R^1$ and $R^2$ are identical - 4-nitro-2-trichloromethylbenzenesulfenic acid chloride is allowed to react with a phosphite of the formula $P(OR^1)_3$  III, where $R^1$ has the above meanings, in an inert solvent and at from −20° to +120° C.

Suitable inert solvents for the reaction are halogenated hydrocarbons, such as carbon tetrachloride, chloroform and methylene chloride, and aromatics, such as toluene and benzene. The preferred temperature range for the reaction is 0° to 100° C.

The 4-nitro-2-trichloromethylbenzenesulfenic acid chloride used as starting material is advantageously prepared by the process described in German Laid-Open Application DE-OS No. 2,460,783 by chlorination of 5-nitrobenzo-1,2-dithio-3-thione in an inert solvent, e.g., carbon tetrachloride, chloroform or dichloroethane, at from −20° to +100° C., preferably +20° to 50° C.

The preparation of the new active ingredients is illustrated in the following examples.

EXAMPLE 1

In a stirred apparatus and at 10° C., 22 g of phosphorous acid dimethyl ester is dissolved in 200 ml of carbon tetrachloride; a solution of 61.4 g of 4-nitro-2-trichloromethylbenzenesulfenic acid chloride in 200 ml of carbon tetrachloride is then added. The mixture is allowed to react for 5 hours at room temperature, and is then heated for 1 hour at 70° C.

After the mixture has cooled it is poured onto 500 g of ice, and the organic phase is separated and washed neutral with water.

After the carbon tetrachloride has been removed in vacuo, there is obtained 70 g (92% of theory) of thiolphosphoric acid-O,O-dimethyl-S-4-nitro-2-trichloromethylphenyl ester as a yellow powder; m.p.: 68° C.

| Analysis | C | H | N | S | Cl | O | P |
|---|---|---|---|---|---|---|---|
| calc.: | 28.2 | 2.5 | 3.7 | 8.4 | 28.2 | 20.9 | 8.3 |
| found: | 28.4 | 2.4 | 3.7 | 8.4 | 28.0 | 21.0 | 8.2 |

The same compound was prepared from 61.4 g of nitro-2-trichloromethylbenzenesulfenic acid chloride and 23.6 g of trimethyl phosphite in toluene. Yield: 90% of theory.

EXAMPLE 2

61.4 g of 4-nitro-2-trichloromethylbenzenesulfenic acid chloride is dissolved in 200 ml of toluene, and the resultant solution dripped, at 10° C., into a solution of 24.2 g of thiophosphorous acid dimethyl ester in 200 ml of toluene. After the mixture has been stirred for 4 hours at room temperature, it is heated for 1 hour at 70° C.

After the mixture has cooled it is poured onto ice, and the organic phase is separated and washed neutral with water. After the toluene has been removed in vacuo, there is obtained 74 g (93% of theory) of dithiophosphoric acid-O,O-dimethyl-S-4-nitro-2-trichloromethylphenyl ester as a pale oil.

| Analysis | C | H | N | S | Cl | O | P |
|---|---|---|---|---|---|---|---|
| calc.: | 27.2 | 2.5 | 3.5 | 16.0 | 26.8 | 16.2 | 7.9 |
| found: | 27.2 | 2.3 | 3.5 | 16.1 | 26.9 | 16.1 | 7.8 |

EXAMPLE 3

At 10° C., 33.2 g of phosphorous acid diethyl ester is dripped into a solution of 61.4 g of 4-nitro-2-trichloromethylbenzenesulfenic acid chloride in 300 ml of toluene. After the mixture has been reacted for 6 hours at room temperature, the toluene is removed in vacuo. There is obtained 65 g (80% of theory) of thiolphosphoric acid-O,O-diethyl-S-4-nitro-2-trichloromethylphenyl ester as a pale oil.

The same compound is obtained analogously in Example 1 from 61.4 g of 4-nitro-2-trichloromethylphenylsulfenic acid chloride and 27.2 g of diethyl phosphite. Yield: 95% of theory.

Analysis

|        | C    | H   | N   | S    | Cl   | O    | P   |
|--------|------|-----|-----|------|------|------|-----|
| calc.: | 32.3 | 3.3 | 3.4 | 8.0  | 26.0 | 19.5 | 7.5 |
| found: | 32.3 | 3.2 | 3.4 | 7.8  | 26.1 | 19.6 | 7.6 |

EXAMPLE 4

At 10° C., a solution of 30.8 g of thiophosphoric acid diethyl ester in 100 ml of benzene is added to 61.4 g of 4-nitro-2-trichloromethylbenzenesulfenic acid chloride in 300 ml of benzene. The mixture is then heated slowly to 70° C. and stirred for 1 hour at this temperature. The mixture is worked up as in Example 2. There is obtained 83 g (98% of theory) of dithiophosphoric acid-O,O-diethyl-S-4-nitro-2-trichloromethylphenyl ester as a pale oil.

Analysis

|        | C    | H   | N   | S    | Cl   | O    | P   |
|--------|------|-----|-----|------|------|------|-----|
| calc.: | 31.0 | 3.0 | 3.4 | 15.0 | 25.3 | 15.2 | 7.4 |
| found: | 31.1 | 3.1 | 3.3 | 15.1 | 25.1 | 15.1 | 7.3 |

The compounds of Examples 5 to 14 are obtained analogously to Example 1.

EXAMPLE 5

Thiolphosphoric acid-O,O-dipropyl-S-4-nitro-2-trichloromethylphenyl ester, pale oil.
Yield: 97% of theory.

Analysis

|        | C    | H   | N   | S   | Cl   | O    | P   |
|--------|------|-----|-----|-----|------|------|-----|
| calc.: | 35.6 | 4.0 | 3.3 | 7.4 | 24.1 | 18.2 | 7.2 |
| found: | 35.7 | 3.9 | 3.2 | 7.3 | 24.4 | 18.3 | 7.1 |

EXAMPLE 6

Thiolphosphoric acid-O,O-diisopropyl-S-4-nitro-2-trichloromethylphenyl ester, pale powder; m.p.: 65° C.
Yield: 97% of theory.

Analysis

|        | C    | H   | N   | S   | Cl   | O    | P   |
|--------|------|-----|-----|-----|------|------|-----|
| calc:  | 35.7 | 3.8 | 3.1 | 7.1 | 24.4 | 18.5 | 7.2 |
| found: | 35.7 | 3.9 | 3.2 | 7.3 | 24.4 | 18.3 | 7.1 |

EXAMPLE 7

Thiolphosphoric acid-O-methyl-O-cyclohexyl-S-4-nitro-2-trichloromethylphenyl ester, pale oil.
Yield: 95% of theory.

Analysis

|        | C    | H   | N   | S   | Cl   | O    | P   |
|--------|------|-----|-----|-----|------|------|-----|
| calc.: | 37.6 | 3.7 | 3.0 | 7.2 | 23.9 | 17.9 | 6.7 |
| found: | 37.5 | 3.8 | 3.1 | 7.1 | 23.8 | 17.8 | 6.9 |

EXAMPLE 8

Thiolphosphoric acid-O,O-di-n-butyl-S-4-nitro-2-trichloromethylphenyl ester, pale oil.
Yield: 97% of theory.

Analysis

|        | C    | H   | N   | S   | Cl   | O    | P   |
|--------|------|-----|-----|-----|------|------|-----|
| calc.: | 38.7 | 4.4 | 3.1 | 7.0 | 22.9 | 17.2 | 6.6 |
| found: | 38.8 | 4.5 | 3.0 | 6.9 | 22.9 | 17.2 | 6.7 |

EXAMPLE 9

Thiolphosphoric acid-O,O-didodecyl-S-4-nitro-2-trichloromethylphenyl ester, pale oil.
Yield: 91% of theory.

Analysis

|        | C    | H   | N   | S   | Cl   | O    | P   |
|--------|------|-----|-----|-----|------|------|-----|
| calc.: | 54.0 | 7.7 | 1.8 | 4.6 | 15.6 | 11.7 | 4.4 |
| found: | 54.0 | 7.7 | 2.0 | 4.6 | 15.5 | 11.6 | 4.5 |

EXAMPLE 10

Thiolphosphoric acid-O-methyl-O-ethyl-S-4-nitro-2-trichloromethylphenyl ester, pale oil.

EXAMPLE 11

Thiolphosphoric acid-O-methyl-O-isopropyl-S-4-nitro-2-trichloromethylphenyl ester, pale oil.

EXAMPLE 12

Thiolphosphoric acid-O-methyl-O-butyl-S-4-nitro-2-trichloromethylphenyl ester, pale oil.

EXAMPLE 13

Thiolphosphoric acid-O,O-dicyclohexyl-S-4-nitro-2-trichloromethylphenyl ester, pale oil.

EXAMPLE 14

Thiolphosphoric acid-O,O-distearyl-S-4-nitro-2-trichloromethylphenyl ester, pale oil.

The compounds of Examples 15 to 19 were prepared analogously to Example 4.

EXAMPLE 15

Dithiophosphoric acid-O,O-dibutyl-S-4-nitro-2-trichloromethylphenyl ester, pale oil.

EXAMPLE 16

Dithiophosphoric acid-O-methyl-O-butyl-S-4-nitro-2-trichloromethylphenyl ester, pale oil.

EXAMPLE 17

Dithiophosphoric acid-O,O-didodecyl-S-4-nitro-2-trichloromethylphenyl ester, pale oil.

EXAMPLE 18

Dithiophosphoric acid-O-ethyl-2-isopropyl-S-4-nitro-2-trichloromethylphenyl ester, pale oil.

EXAMPLE 19

Dithiophosphoric acid-O-dicyclohexyl-S-4-nitro-2-trichloromethylphenyl ester, pale oil.

The new compounds exhibit a good fungicidal action and are well tolerated by crop plants. They are suitable for combating phytopathogenic soil-borne fungi, e.g., Pythium, Aphanomyces and Fusarium species, which cause diseases in the emergence and seedling stages in Leguminosae, lettuce, beets, cotton and other crop plants. The novel compounds may also be used to combat injurious fungi which attack and destroy plant parts above ground; they are particularly suitable for combating *Pyricularia oryzae* in rice.

The agents according to the invention may suppress simultaneously the growth of 2 or more of the above fungi. Application rates necessary for combating phytopathogenic fungi are from 0.05 to 5 kg of active ingredient per hectare.

Further, the new active ingredients are suitable for protecting wood in stock and wood already in use in construction against attack or rotting by wood-destroying fungi from the Basidiomycetes class, e.g., *Coniophora puteana, Serpula lacrymans, Poria monticola, Lenzites trabea, Trametes versicolor, Armillaria mellea*, and *Fomes annosus*.

The active ingredients of the invention can be converted into the conventional formulations, e.g. solutions, emulsions, suspensions, dusts, powders, pastes and granules. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents contain from 0.1 to 95 percent by weight of active ingredient, preferably from 0.5 to 70 percent.

The application rates depends on the type of effect desired, and is from 0.05 to 5 kg of active ingredient per hectare.

The formulations, and the ready-to-use preparations obtained therefrom, e.g., solutions, emulsions, suspensions, powders, dusts, pastes or granules, are applied in the conventional manner, e.g. by spraying, atomizing, dusting, treating seed, or watering.

Examples of such formulations are as follows:

I. 90 parts by weight of the compound of Example 1 is mixed with 10 parts by weight of N-methyl-α-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 1 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of the compound of Example 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of the compound of Example 6 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of the compound of Example 9 is intimately mixed with 97 parts by weight of particulate kaolin. A dust is obtained containing 3% by weight of the active ingredient.

VII. 30 parts by weight of the compound of Example 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 3 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt % of active ingredient.

IX. 20 parts of the compound of Example 4 is intimately mixed with 2 parts of the calcium salt of dodecylbenzensulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

X. To prepare an oily wood preservative containing 1% of active ingredient, 1 part of the compound of Example 1 is mixed with 15 parts of an alkyl resin having a medium oil content (20% solid resin). 45 parts of an aromatics-containing gasoline fraction is then added, and the mixture is, if desired, filtered to remove impurities, and made up to 100 parts with an aliphatics-containing gasoline fraction.

Oily wood preservatives containing 2% of active ingredient are prepared analogously.

The above ready-to-use preparations may contain other active ingredients together with those according to the invention, e.g. herbicides, insecticides, growth regulators and other fungicides or may be mixed with fertilizers and applied together with these. Mixture with other fungicides often broadens the spectrum of fungicidal action. Synergistic effects also occur with a number of these fungicidal mixtures, i.e., the fungicidal action of the combination product is greater than that of the individual components added together.

The following list of fungicides with which the compounds according to the invention may be combined is intended to illustrate and not restrict the combination possibilities. Examples of fungicides which can be combined with the compounds of the invention are:

ferric dimethyldithiocarbamate (ferbam)
zinc dimethyldithiocarbamate (ziram)
manganese ethylenebisdithiocarbamate (maneb)
zinc ethylenebisdithiocarbamate (zineb)
tetramethylthiuram disulfide (thiram)
3,5-dimethyl-1,3,5-2H-tetrahydrothiadiazine-2-thione
manganese-zinc ethylenediamine-bisdithiocarbamate (mancoceb)
zinc-(N,N'-propylene-bisdithiocarbamate) (propineb)
ammonia complex of zinc-(N,N'-ethylene-bisdithiocarbamate)
and
N,N'-polyethylene-bis-(thiocarbamoyl)-disulfide (metiram)
ammonia complex of zinc-(N,N'-propylene-bisdithiocarbamate) and
N,N'-polypropylene-bis-(thiocarbamoyl)-disulfide (methyl-metiram)
dinitro-(1-methylheptyl)-phenylcrotonate (dinocap)
2-sec-butyl-4,6-dinitrophenyl-3,5-dimethylacrylate (binapacryl)
2-sec-butyl-4,6-dinitrophenylisopropylcarbonate
2,4,5-trichlorophenol
pentachlorophenol (PCP)
barium salt of pentachlorophenol (5B)
pentachlorophenyl acetate
pentachlorobenzyl alcohol
di-(5-chloro-2-hydroxyphenyl)-methane (dichlorophen)
phenyl-(5-chloro-2-hydroxyphenyl)-methane
N-trichloromethylthiotetrahydrophthalimide (captan)
N-trichloromethylthiophthalimide (folpet)
N-(1,1,2,2-tetrachloroethylthio)-tetrahydrophthalimide (captafol)
2-heptadecyl-2-imidazoline acetate (glyodin)
2,4-dichloro-6-(o-chloroanilino)-s-triazine (anilazin)
O,O-diethylphthalimidophosphorothioate (plondrel)
5-amino-1-[bis-(dimethylamino)-phosphinyl]-3-phenyl-1,2,4-triazole
5-ethoxy-3-trichloromethyl-1,2,4-thiadiazole
2,3-dicyano-1,4-dithiaanthraquinone (dithianon)
2,3-quinoxalinedithiol cyclic trithiocarbonate (thioquinox)
methyl 1-(butylcarbamoyl)-2-benzimidazole carbamate (benomyl)
2-methoxycarbonylaminobenzimidazole
2-thiocyanomethylthiobenzothiazole (busan)
4-(2-chlorophenylhydrazono)-3-methyl-5-isooxazolone
1-(1,2,4-triazolyl-1')-1-(4'-chlorophenoxy)-3,3-dimethylbutan-2-one (triadimefon)
1-(1-imidazoyl)-2-allyloxy-2-(2,4-dichlorophenyl)-ethane (imazalil)
2-(O,O-diethylthionophosphoryl)-5-methyl-6-carbethoxypyrazolo-(1,5a)-pyrimidine (pyrazophos)
pyridine-2-thiol-1-oxide
8-hydroxyquinoline and its copper salt
5,5-dimethyl-3-(3,5-dichlorophenyl)-2,4-dioxo-1,3-oxazolidine
5-methyl-5-vinyl-3-(3,5-dichlorophenyl)-2,4-dioxo-1,3-oxazolidine
2-[furyl-(2)]-benzimidazole
piperazine-1,4-diyl-bis[1-(2,2,2-trichloroethyl)-formamide] (triforine)
2-[thiazolyl-(4)]-benzimidazole
5-butyl-2-dimethylamino-4-hydroxy-6-methylpyrimidine (dimethirimol) bis-(p-chlorophenyl)-3-pyridinemethanol
1,2-bis-(3-ethoxycarbonyl-2-thioureido)-benzene (thiophanat)
1,2-bis-(3-methoxycarbonyl)-2-thioureido)-benzene (thiophanat M) dodecylguanidine acetate (dodine)
3-[2-(3,5-dimethyl-2-oxycyclohexyl)-2-hydroxyethyl]-glutarimide (cycloheximide)
hexachlorobenzene
N-dichlorofluoromethylthio-N,N'-dimethyl-N-phenyl-sulfuric acid diamide (dichlorfluanid)
N-dichlorofluoromethylthio-N-methyl-N'-methyl-N'-phenylsulfuric acid diamide
2,4,5,6-tetrachloroisophthalonitrile (daconil)
1-(3,4-dichloroanilino)-1-formylamino-2,2,2-trichloroethane (chloraniformethan)
2,6-dimethyl-N-tridecylmorpholine and its salts
2,6-dimethyl-N-cyclododecylmorpholine and its salts
2,3-dichloro-1,4-naphthoquinone
1,4-dichloro-2,5-dimethoxybenzene
p-dimethylaminobenzenediazosodium sulfonate
2-chloro-1-nitropropane
polychloronitrobenzenes such as pentachloronitrobenzene
methyl isothiocyanate
triphenyltin acetate (fentin acetate)
fungicidal antibiotics such as griseofulvin and kasugamycin
methyl-N-(2,6-dimethyl)-N-(2-furoyl)-alaminate
methyl-N-(2,6-dimethyl)-N-(2-methoxyacetyl)-alaminate
mercaptobenzothiazole
2-cyano-N-[(ethylamino)-carbonyl]-2-(methoximino)-acetamide
β-(4-chlorophenxy)-α-(1,1-dimethyl)-1H-1,2,4-triazole-1-ethanol
benzisothiazolone
tetrafluorodichloroacetone
1-phenylthio semicarbazide
N-nitrosocyclohexylhydroxylamine and its aluminum salt (fungol)
Bordeaux mixture
nickel-containing compounds sulfur.

These agents may be added to the fungicides according to the invention in a weight ratio of from 1:10 to 10:1. If desired, they need not be added until immediately before use (tankmix).

Examples A, B and C below demonstrate the biological action of the new compounds. The substances employed for comparison purposes were cis-N-[(trichloromethyl)-thio]-4-cyclohexene-1,2-dicarboximide (Y) (Chem. Week, June 21, 1972, p. 46) and thiolphosphoric acid-O,O-diethyl-S-benzyl ester (Z) (U.S. Pat. No. 3,274,051).

A. 100 g samples of pea seeds of the "Senator" variety are carefully shaken for about 5 minutes in glass bottles with 300 mg (=0.3 wt%) of seed disinfectant formulations containing (dry basis) 40% of active ingredient. Subsequently, 100 seeds are sown 3 cm deep and 3 to 5 cm apart in seed boxes in a compost naturally and heavily infested with the fungi Pythium spec., Aphanomyces spec. and *Fusarium oxysporum*. The boxes are set up in the greenhouse at from 17° to 20° C. The number of healthy pea plants is determined after 21 days.

| Compound from Ex. no. | Percentage of healthy plants after 21 days in compost |
| --- | --- |
| 2 | 96 |
| 8 | 92 |
| 9 | 85 |
| Y | 70 |
| Control (untreated) | 18 |
| Control (untreated) in sterilized compost | 94 |

B. Leaves of pot-grown rice seedlings are artificially infected with an aqueous conidial suspension of the fungus *Pyricularia oryzae*. The plants are then placed for 24 hours in a chamber kept at 22° to 25° C. and having high humidity (steam saturation); after this time, they are sprayed to runoff with a 0.1 wt % aqueous emulsion containing (dry basis) 80% of active ingredient and 20% of dispersant. The pots are then returned to the chamber. After 5 days, the disease symptoms on the untreated control plants have spread to such an extent that the leaf blotches which have formed cover almost the entire surface.

Fungus attack is assessed as follows:
0=no attack, graduated down to 5=heavy attack

| Compound from Ex. no. | Leaf attack after spraying with 0.1% formulation |
| --- | --- |
| 4 | 1 |
| 7 | 1 |
| 9 | 0 |
| Z | 2 |
| Control (untreated) | 5 |

C. To determine the activity on the wood-destroying fungi *Coniophora puteana* and *Trametes versicolor*, the procedure adopted was substantially in accordance with DIN 25,176, Sheet 1, "Prüfung von Holzschutzmitteln, Mykologische Kurzprüfung (Klötzchenverfahren") (="Testing of wood preservatives, mycological short-term test (block process)"): pine sapwood blocks measuring 50×25×15 mm were coated at a rate of 200 g/m² of wood surface with oily wood preservative formulations containing 1 and 2% of active ingredient. After the treated blocks had been stored for 4 weeks, they were placed, together with untreated blocks, in glass dishes containing the fungi *Coniophora puteana* or *Trametes versicolor* in a nutrient agar. The dishes were then incubated in an atmospheric laboratory at 22° C. and a relative humidity of 70%. After 3 months, the fungus mycelium attaching to the blocks was removed and the blocks were dried. The degree of wood destruction was then ascertained in accordance with the scale given in the DIN specification.

| Compound from Ex. no. | Percentage of compound in formulation | Degree of fungus attack after 3 months | |
| --- | --- | --- | --- |
| | | *Coniophora puteana* | *Trametes versicolor* |
| 1 | 1 | 1 | 1 |
| 2 | 2 | 1 | 1 |
| 3 | 1 | 1 | 1 |
| | 2 | 1 | 1 |
| 5 | 1 | 1 | 1 |
| | 2 | 1 | 1 |
| Control (only solvent; no active ingredient) | — | 3a/4b | 3b |

Assessment scale
1 undamaged
2a slight attack in parts
2b slight attack all over
3a heavy attack in parts
3b heavy attack all over
4a completely destroyed in parts
4b completely destroyed all over.

We claim:

1. A tholphosphoric acid-S-4-nitro-2-trichloromethylphenyl ester of the formula

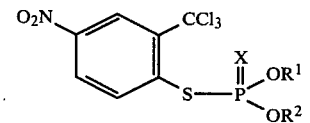

where X denotes oxygen or sulfur, and $R^1$ and $R^2$ are identical or different and each denotes unsubstituted alkyl groups of 1 to 18 carbon atoms, substituted alkyl groups of 1 to 18 carbon atoms containing as substituents halogen or alkoxyl of 1 to 4 carbon atoms and unsubstituted cycloalkyl radicals of 5 to 18 carbon atoms and substituted cycloalkyl radicals of 5 to 18 carbon atoms containing as substituents halogen or alkoxyl of 1 to 4 carbon atoms.

2. A fungicidal composition comprising a liquid or solid diluent and a fungicidally effective amount of at least one compound as set forth in claim 1.

3. A compound selected from the group consisting of thiolphosphoric acid-O,O-dimethyl-S-4-nitro-2-trichloromethylphenyl ester, dithiophosphoric acid-O,O-dimethyl-S-4-nitro-2-trichloromethylphenyl ester, thiolphosphoric acid-O,O-diethyl-S-4-nitro-2-trichloromethylphenyl ester, dithiophosphoric acid-O,O-diethyl-S-4-nitro-2-trichloromethylphenyl ester, thiolphosphoric acid-O,O-dipropyl-S-4-nitro-2-trichloromethylphenyl ester, thiolphosphoric acid-O-methyl-O-cyclohexyl-S-4-nitro-2-trichloromethylphenyl ester, thiolphoshoric acid-O,O-di-n-butyl-S-4-nitro-2-chloromethylphenyl ester, and thiolphosphoric acid-O,O-didodecyl-S-4-nitro-2-trichloromethylphenyl ester.

4. A fungicidal composition comprising a liquid or solid diluent and a fungicidally effective amount of at least one compound as set forth in claim 3.

* * * * *